United States Patent [19]

Foos et al.

[11] Patent Number: 5,702,575
[45] Date of Patent: Dec. 30, 1997

[54] METHOD OF PREPARING AN ELECTROCHEMICAL PLANAR METAL/METAL OXIDE ELECTRODE

[75] Inventors: Joseph S. Foos, Needham; John S. Benco, Holliston, both of Mass.

[73] Assignee: Chiron Diagnostics Corporation, E. Walpole, Mass.

[21] Appl. No.: 551,596

[22] Filed: Nov. 1, 1995

Related U.S. Application Data

[63] Continuation-in-part of Ser. No. 379,405, Jan. 27, 1995, abandoned.
[51] Int. Cl.$^6$ ........................................ C25B 11/04
[52] U.S. Cl. .................... 204/292; 204/291; 204/435; 204/280; 423/22; 423/23; 423/35; 423/84
[58] Field of Search ........................ 204/412, 435, 204/280, 291, 292; 423/22, 23, 35, 84

[56] References Cited

U.S. PATENT DOCUMENTS

| | | | |
|---|---|---|---|
| 3,462,353 | 8/1969 | Every et al. | 204/435 |
| 4,007,106 | 2/1977 | Hone et al. | 204/422 |
| 4,536,274 | 8/1985 | Papadakis et al. | 204/433 |
| 4,571,292 | 2/1986 | Liu et al. | 204/412 |
| 4,734,184 | 3/1988 | Burleigh et al. | 204/409 |
| 5,030,331 | 7/1991 | Sato | 205/107 |
| 5,110,441 | 5/1992 | Kinlen et al. | 204/418 |
| 5,494,562 | 2/1996 | Maley et al. | 204/412 |

FOREIGN PATENT DOCUMENTS 0625704  11/1994  European Pat. Off. .

OTHER PUBLICATIONS

Inorganic Chem. (Ephraim 1943) Oxides of Noble Metals pp. 462–463.

Glab, S., et al., "Metal–Metal Oxide and Metal Oxide Electrodes as pH Sensors," *Critical Reviews in Analytical Chemistry*, vol. 21, pp. 29–47 (1989). No Month Available.

Kinoshita, E., et al., "An Examination of the Palladium/Palladium Oxide System and its Utility for pH–Sensing Electrodes," *Electrochimica Acta*, vol. 31, No. 1, pp. 29–38 (1996), No Month Available.

Grubb, W.T., et al., "Palladium–Palladium Oxide pH Electrodes," *Analy. Chem.*, vol. 52, pp. 270–273 (1980), No Month Available.

Liu, C–C., et al., "A Palladium–Palladium Oxide Miniature pH Electrode," *Science*, vol. 207, pp. 188–189 (Jan. 11, 1980).

Coon, R.L., et al., "Evaluation of a Dual—Function pH and $PCO_2$ in Vivo Sensor," *J. of Applied Physiology*, vol. 40., No. 4, pp. 625–629 (Apr. 1976).

Oubda, S.T., et al., "Thin Film IRO2–Electrodes Modified by Pt–Nucleation Processes: Their Application for Construction of a pH and Glucose Sensor," Extended Abstracts of the Spring Meeting of the ECS, Honolulu, 93–1, Abstract No., 1705, pp. 2332–2333 (1993), No Month Available.

Pedigo, J.L., et al., "Printer's Primer," *Hybrid Circuit Technology*, pp. 28–31, (Feb. 1992).

Covington, A.K., ed., *Ion Selective Electrode Methodology*, vol. 1, CRC Press, Inc., pp. 32–33 (1979), No Month Available.

*Primary Examiner*—Bruce F. Bell
*Attorney, Agent, or Firm*—Arthur S. Morganstern; Stanley Sacks; Robert P. Blackburn

[57] ABSTRACT

An improved active electrode for use in planar sensors has been discovered, the electrode prepared by a process comprising combining a base component with a metal paste and heating the paste in the presence of air for a time sufficient to oxidize a portion of the electrode to produce the metal/metal oxide electrode. The electrodes may be incorporated into various planar sensor formats, particularly pH and $CO_2$ sensors.

9 Claims, 7 Drawing Sheets

METHOD OF PREPARING AN ELECTROCHEMICAL PLANAR METAL/METAL OXIDE ELECTRODE

This application is a continuation-in-part of application Ser. No. 08/379,405 filed on Jan. 27, 1995 now abandoned.

FIELD OF THE INVENTION

This invention relates to a planar metal/metal oxide active electrode that may be employed in sensors that measure pH and/or $CO_2$.

Electrochemical means for measuring the pH and $CO_2$ levels of liquid systems are well known. Glass sensors having membrane type of electrodes are commonly used as standards for pH and $CO_2$ measurements because glass sensors are predictable and provide good measuring capability. Glass sensors are fabricated as three-dimensional articles, with many serviceable parts. Thus, while demonstrating good measuring capability, these three-dimensional articles are more expensive and complex to manufacture as well as operate as compared to planar format sensors.

Planar format sensors have been described in the literature (such as those taught by Foos et al., EP-A0625704, hereby incorporated by reference) and provide an alternative means to measuring pH and $CO_2$ levels. Planar sensors are typically smaller than glass sensors and much cheaper to manufacture as well as operate. The planar format of the sensors typically comprises relatively thin layers of materials which are applied to substrate bases using thick-film or thin-film techniques, including, for example, silk-screen printing.

Planar sensors for the measurement of pH and $CO_2$ are more economically desirable than glass sensors, but planar sensors have been associated with performance problems. Limitations of planar pH sensors include, for example, drift in potential requiring frequent recalibrations; oxygen ($O_2$) interference (which can give incorrect answers due to varying levels of $O_2$); sensitivity to reduction or oxidation (redox) agents; and short lifetime of sensor, particularly due to contamination by sample components or impurities present in other sensor components.

Improvement in the performance of planar sensors is needed in order to make the sensors more commercially desirable and well accepted as an alternative means for measuring pH and $CO_2$.

SUMMARY OF THE INVENTION

The problem noted above has been solved with the discovery of an improved active metal/metal oxide electrode, the active metal/metal oxide electrode prepared by a process comprising combining a base component with a metal paste to form a metal paste mixture, heating the metal paste mixture in the presence of air for a time sufficient to oxidize a portion of the mixture to form said metal/metal oxide electrode.

A planar sensor for the measurement of pH is also provided, the sensor comprising an electrically nonconductive substrate having applied thereto in a planar format: an electrically conductive material in at least one region adjacent to said substrate; a dielectric coating covering at least a lead portion of said region of said electrically conductive material but leaving exposed at least an electrode area and a contact area on said region of said electrically conductive material; and a metal/metal oxide electrode in said exposed electrode area, wherein said metal/metal oxide electrode is prepared by a process comprising combining a base component with a metal paste to form a metal paste mixture, heating the metal paste mixture in the presence of air for a time sufficient to oxidize a portion of the mixture to form said metal/metal oxide electrode.

A method for preparing a pH sensor is also provided, the method comprising: (1) selecting an electrically nonconductive substrate; (2) adheringly applying thereto in a planar format: an electrically conductive material in at least one region adjacent to said substrate; a dielectric coating covering at least a lead portion of said electrically conductive region but leaving exposed at least an electrode area and a contact area of said electrically conductive region; and a metal/metal oxide electrode present on said exposed electrode area, wherein said metal/metal oxide electrode is prepared by a process comprising combining a base component with a metal paste to form a metal paste mixture, heating the metal paste mixture in the presence of air for a time sufficient to oxidize a portion of the mixture to form said metal/metal oxide electrode.

A method for measuring pH in a sample has also been discovered, the method comprising contacting a liquid sample with the planar pH sensor described above and a reference, connecting said exposed contact area of said sensor with a pH sensing instrument; connecting said reference with said pH sensing instrument providing an electrical current from said pH sensing instrument through said reference and said contact area of said sensor, and measuring a resulting electrical signal provided by said pH sensing instrument.

A $CO_2$ planar sensor for the measurement of $CO_2$ has also been discovered, the sensor comprising an electrically nonconductive substrate having adheringly applied thereto in a planar format: (a) an electrically conductive material in at least a first and second region adjacent to said substrate (b) a dielectric coating covering at least a lead portion of said first and second regions of said electrically conductive material but leaving exposed at least an electrode area and a contact area on said first and second regions (c) a silver/silver halide electrode in said exposed electrode area of said first electrically conductive region; (d) a metal/metal oxide electrode in said exposed electrode area of said second electrically conductive region, said metal/metal oxide electrode prepared by a process comprising combining a base component with a metal paste to form a metal paste mixture, heating the metal paste mixture in the presence of air for a time sufficient to oxidize a portion of the mixture to form said metal/metal oxide electrode; (e) an internal electrolyte layer applied adjacent to and superimposed over at least said metal/metal electrode and said silver/silver halide electrode; and (f) a gas permeable membrane adjacent to and superimposed over said internal electrolyte in at least the portion of said electrolyte layer covering said metal/metal oxide electrode and said silver/silver halide electrode.

A method for preparing a $CO_2$ planar sensor is also provided, the method comprising: (1) selecting an electrically nonconductive substrate; (2) adheringly applying thereto in a planar format: (a) an electrically conductive contact material in at least separate first and second regions; (b) a dielectric coating separating said first and second regions of said electrically conductive contact material, said dielectric coating covering at least a lead portion of said first and second regions of said electrically conductive material but leaving exposed at least an electrode area and a contact area on said first and second regions; (c) a silver/silver halide electrode in said exposed electrode area of said first electrically conductive region; (d) a metal/metal oxide electrode in said exposed electrode area of said second electrically conductive region, said metal/metal oxide electrode prepared by a process comprising combining a base component with a metal paste to form a metal paste mixture, heating the metal paste mixture in the presence of air for a time sufficient to oxidize a portion of the mixture to form said metal/metal oxide electrode; (e) an internal electrolyte layer applied adjacent to and superimposed over at least said formed metal/metal electrode and said silver/silver halide electrode; and (f) a gas permeable membrane adjacent to and superimposed over said internal electrolyte in at least the portion of said electrolyte layer covering said metal/metal oxide electrode and said silver/silver halide material.

A method for measuring $CO_2$ in a sample has also been discovered, the method comprising: contacting a liquid sample with the $CO_2$ sensor described above, connecting said exposed contact area of said first and second electrically conductive regions of said sensor with a $CO_2$ sensing instrument, providing an electrical current from said $CO_2$ sensing instrument through said contact areas, measuring an electrical signal provided by said $CO_2$ sensing instrument.

The invention provides an economical method of manufacturing planar pH and $CO_2$ sensors capable of accurate measurement of pH and $CO_2$ in sample fluids. Sensors that have been prepared using this electrode show a good response top pH or $CO_2$ while demonstrating minimal drift and $O_2$ interference.

DETAILED DESCRIPTION

Figure 2A:
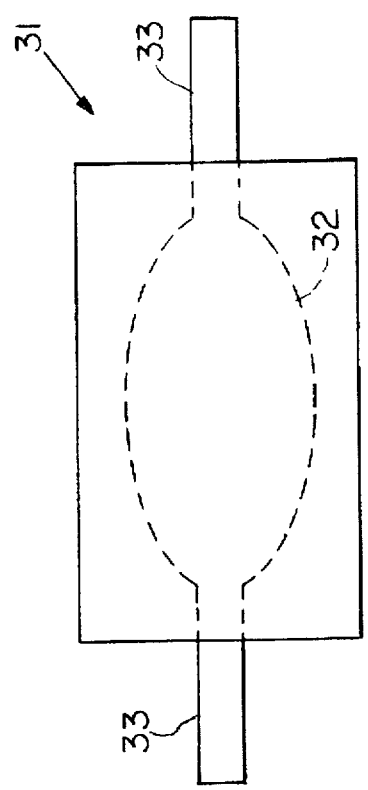
FIGS. 2a and 2b show a top view (2a) and a side view (2b) of a sample chamber.

The invention is suitable for use in determining the pH and/or $CO_2$ of liquid samples. The invention is particularly useful for measuring the pH and/or $CO_2$ of biological fluids. Non-liquid samples may be prepared as liquid samples and thereafter tested, as known to those skilled in the art. The pH range that may be measured by the invention may vary greatly, with particular sensitivity realized for a pH measurement of from a pH of 3 to pH of 11.

According to the invention, in preparing the metal/metal oxide electrode, the metal paste may be purchased or prepared by known techniques. Preferably the paste is of a thixotropic consistency (such the paste will flow) but is not of a thin, runny consistency. The appropriate consistency of the paste may be easily determined by those skilled in the art of preparing planar formatted sensors. The metals that may be used in the preparation of the active electrode are noble metals as described, for example, in "Metal-Metal Oxide and Metal Oxide Electrodes as pH Sensor" by S. Glab, et al, *Crit. Rev. Anal. Chem.* 21, 29–47, 1989. Suitable metals include, but are not limited to, palladium, rhodium, ruthenium, osmium, iridium, platinum, tin, antimony, bismuth, alloys thereof, and mixtures thereof. More preferably the metal is palladium or iridium, most preferably, palladium.

A base component is combined with the metal paste to form the metal paste mixture that goes to form the metal/metal oxide electrode. The base selected must be capable of generating a metal/metal oxide when the metal paste and base combination is heated. Preferably the base is a salt, such as, for example salts of an alkali metal (lithium, sodium, potassium, rubidium, and so on) and salts of an alkali earth metal (beryllium, magnesium, calcium, and so on). More preferably, the salt is non-hydroscopic, i.e. a salt that remains in a particulate form at ambient conditions. Preferred non-hydroscopic salts are represented by "MHB" and "MB", wherein M is defined as an alkali earth metal or alkali metal, H is hydrogen, and B is an anion selected from the group consisting of —$CO_3$, —OH, and —$HCO_3$ (including, for example, $Na_2CO_3$, $NaHCO_3$, $K_2CO_3$, $KHCO_3$, $MgCO_3$, and mixtures thereof). The most preferred base component is $NaHCO_3$. The base component is most preferably a fine particulate such that when screen printing is the technique used for fabricating the planar sensor, the particulate does not exceed the mesh size of the screen (typically less than about 400 mesh size). The base should be used in an amount sufficient to provide an oxidizing effect when the metal paste mixture are heated in the presence of air, but not in such an excessive amount as to compromise the consistency of the paste for planar formatting. Generally, the base is used in an amount ranging from about 0.1 wt. % to about 50 wt. %, more preferably, in an amount ranging from 5 wt. % to 25 wt. %, and most preferably about 16 wt. %, with said weight percentages based on the total weight of the metal paste and base prior to heating. The metal paste and base may be combined prior to or during the planar formatting process. Additionally, the metal paste mixture may be heated in the presence of air to produce a metal/metal oxide electrode prior to placement on an electrically nonconductive substrate. For ease of manufacturing, preferably the metal paste and base are combined, mixed, and then applied to an electrically conductive contact material present on the nonconductive substrate and thereafter heated. The manner in which the metal paste mixture is applied to the electrically conductive contact material on the substrate may be any suitable technique resulting in a planar format, including stenciling, and known thin or thick film processes (such as described in J. L. Pedigo, et al., *Hybrid*

*Circuit Technology*, February 1992, pp. 28–31, hereby incorporated by reference). Particularly from an ease of manufacturing standpoint, silk screen printing is a preferred means to apply the metal paste mixture to the substrate. The thickness of the metal paste mixture may be varied.

The substrate materials that make up the base support upon which the sensors are fabricated may be selected from any electrically non-conductive material. These materials are well-known and include, for example, ceramic, glass, refractory, and polymeric materials, and combinations thereof, and so on. Particularly preferred are alumina based substrate chips. Currently, most preferred substrates are of an alumina and glass binder combination. Groves may be fashioned in the nonconductive substrate such that layers N can be specifically applied to sections on the substrate.

The electrically conductive material used in the sensors is preferably a noble metal, with gold most preferred. The electrically conductive material may be applied to the substrate in various ways, although most preferably the material is adhered to the substrate, typically by heating, prior to applying the dielectric coating and metal paste mixture. Typically for pH sensors, at least one region of the electrically conductive material is applied to the substrate. For $CO_2$ sensors, at least two separate regions of the electrically conductive material are applied to the substrate. Preferably a dielectric coating is present between the two regions on the $CO_2$ sensor thus insulating the conductive regions from each other. Typically the dielectric coating (as widely commercially available) is also present on at least the lead portions of the electrically conductive regions but is not present on an exposed electrode area and an exposed contact area in each region of the conductive material. The metal paste mixture is applied adjacent to the electrically conductive region in at least the exposed electrode area.

The metal paste is heated at a temperature and for a period sufficient to oxidize a portion of the metal paste mixture thus forming a metal/metal oxide electrode. As oxygen may typically be present in the base component, oxygen does not have to be present during the heating. Preferably, however, the heating occurs in the presence of oxygen (most conveniently air). The time and temperature of heating may be adjusted according to the type of heating source employed, the temperature employed, and the time of exposure. Preferably, the metal paste mixture is heated for a period sufficient to provide an active electrode having an equilibrium of metal to metal oxide content, such as described in S. Glab, et al. (referenced previously herein). More preferably, to transform the metal oxide paste to a metal/metal oxide electrode (preferably present on the substrate), the paste is heated for a period of from about 1 min. to 30 min. (more preferably 5 min. to 15 min.) at a temperature of from about 450° C. to about 600° C. (more preferably from 525° C. to 575° C.) to oxidize a portion (but not all) of the electrode. Additionally the electrode may be reheated during the fabrication of the entire sensor if desired.

The active metal/metal oxide electrode may be used in different types of sensors, most preferably planar pH and $CO_2$ sensors. Components described herein, as well as additional features, may e arranged in the planar format on non-conductive substrates in various configurations.

Figure 1:
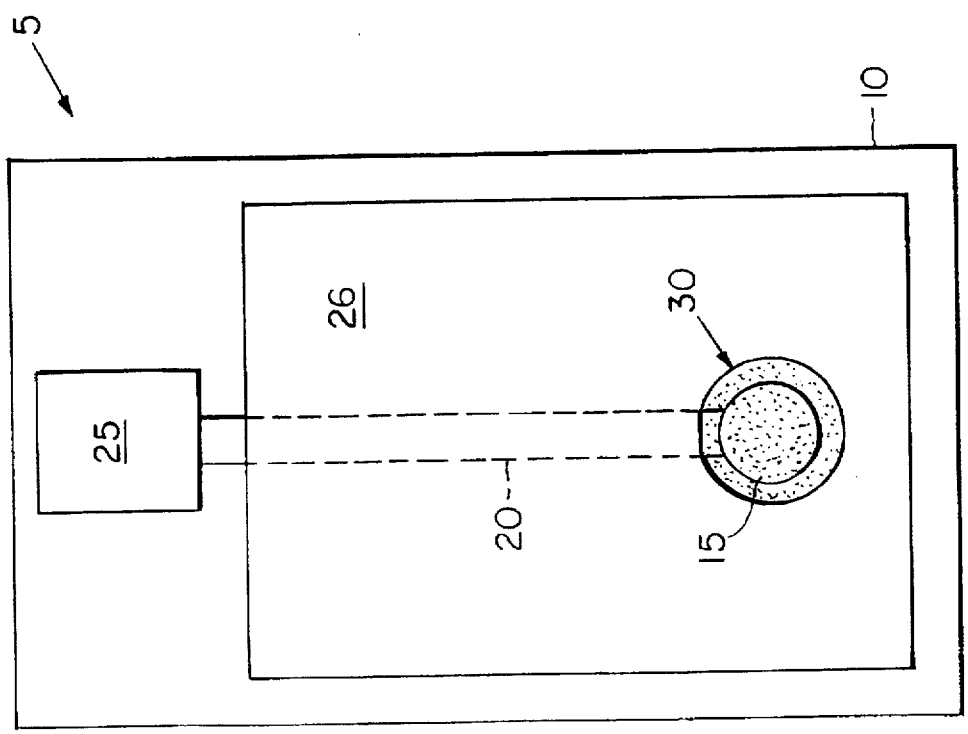
FIG. 1 shows a metal/metal oxide planar sensor prepared according to the invention.

As shown in the FIG. 1, a pH sensor 5 is present on an electrically nonconductive substrate 10 having present thereon an electrically conductive material in one region 15, 20, 25 adheringly applied adjacent to the substrate 10. The insulating dielectric coating 26 is applied over the substrate and electrically conductive lead portion 20 but not over an exposed electrode area 15 and an exposed contact area 25. In the exposed electrode area 15, the metal paste mixture is applied and becomes the metal/metal oxide active electrode 30 upon heating in the presence of air. The exposed contact area 25 is where electrical contact may be made between the sensor 5 and the pH sensing instrument.

As shown in FIG. 2a (top view) and 2b (side view), a sample chamber 31 may be superimposed upon the active electrode area 15, 30 of the sensor 5 so that the fluid sample enters and exits through the sample tube 33 and is confined in a sample chamber contact region 32 such that contact is made between the sample and the active electrode 30 (and reference electrode when present in the sensor chip). Alternatively, the sensor 5 may directly immersed in a fluid sample such that a sample chamber is not part of the configuration of the sensor.

Figure 3:
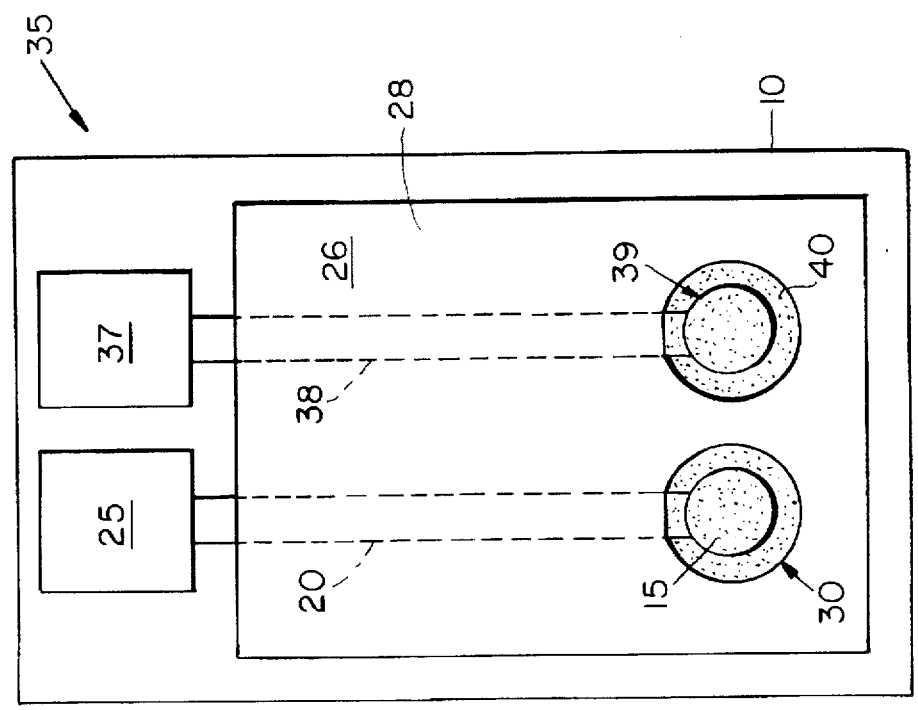
FIG. 3 shows a Severinghaus $CO_2$ type sensor.

FIG. 3 shows a Severinghaus type of sensor 35 that may be used in the measurement of $CO_2$. This sensor 35 differs from the pH sensor 5 by having an additional region of electrically conductive material 37, 38, 39 with an exposed active electrode area 39 (with no dielectric coating) having present thereon a silver/silver halide material 40 that is used as an internal reference electrode. The second region of electrically conductive material also has present an exposed contact area 37 and a dielectric coating 26 over a lead portion of the electrically conductive material. The metal/metal oxide electrode area 15, 30; lead 20; and contact area 25 are insulated from the silver/silver halide electrode 39, lead 38, and contact area 37 that form the internal reference electrode by the dielectric coating. In the Severinghaus sensor 35, the mV output between the metal/metal oxide electrode 30 and the silver/silver halide electrode 39 is linearly related to log $pCO_2$. Preferably the halide of the internal reference electrode is chloride. The silver/silver halide electrode may be pro-formed and plated on at least the exposed electrode area of the conductive material of substrate or may be applied as a paste and thereafter heated to form the silver/silver halide electrode.

Figure 4:
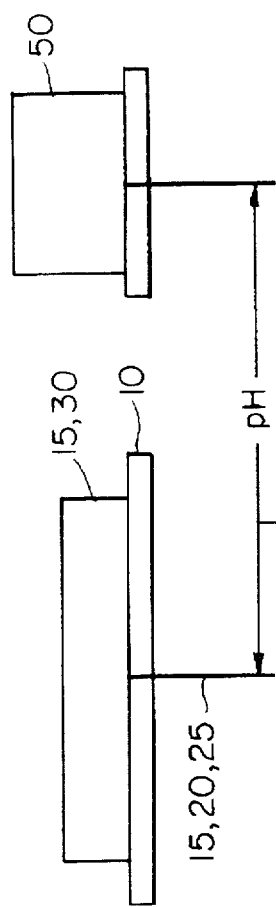
FIG. 4 shows a planar sensor having a metal/metal oxide electrode and a reference electrode.

In FIG. 4, a pH sensor is shown where electrical contact between the active electrode 30, reference electrode 50, and sensing equipment (or instrument) 55 is made using the electrically conductive regions 15, 20, 25 of the sensor thereby resulting in a measurement of the pH.

Figure 5:
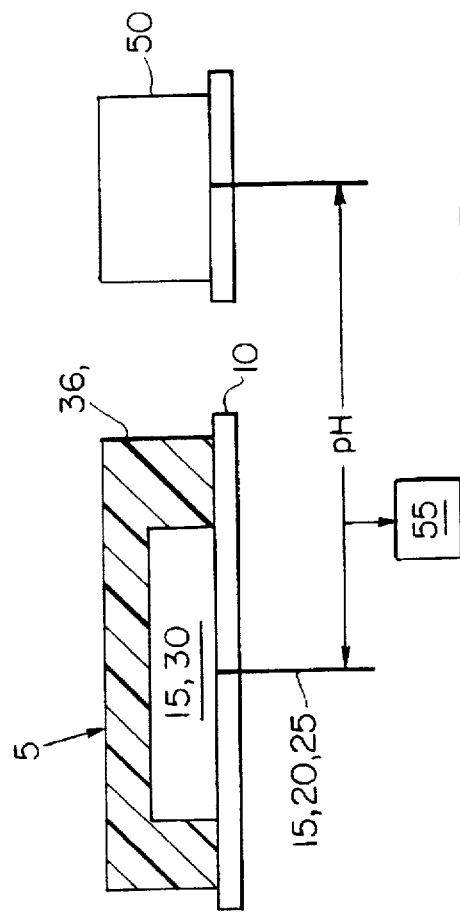
FIG. 5 shows a planar sensor having a metal/metal oxide electrode with a cover membrane and a reference electrode.

As shown in FIG. 5, the pH sensor may have present a neutral carrier cover membrane 36. When present on the pH sensor, the cover membrane functions to protect the active electrode from the outside environment and materials which degrade the performance of the sensor, such as redox centers and biological materials. As defined herein, the neutral carrier cover membrane itself is capable of sensing the concentration of the pH, where the protons do not go through during the measurement of pH but rather establish a potential across the cover membrane. The cover membrane may be applied to the planar sensor in various ways, including dip coating, and so on. Materials that may be used to prepare the cover membrane are well-known water permeable and gas permeable polymeric materials known to those skilled in the art. Particularly preferred polymeric or copolymeric materials that may be used include polyvinyl halide monomers. More preferably employed as the major component of the cover membrane is a polyvinyl chloride (more preferably a plasticized polyvinyl chloride). Other components that are typically included in the cover membrane are known ioniphores and lipophilic salts.

Figure 6:
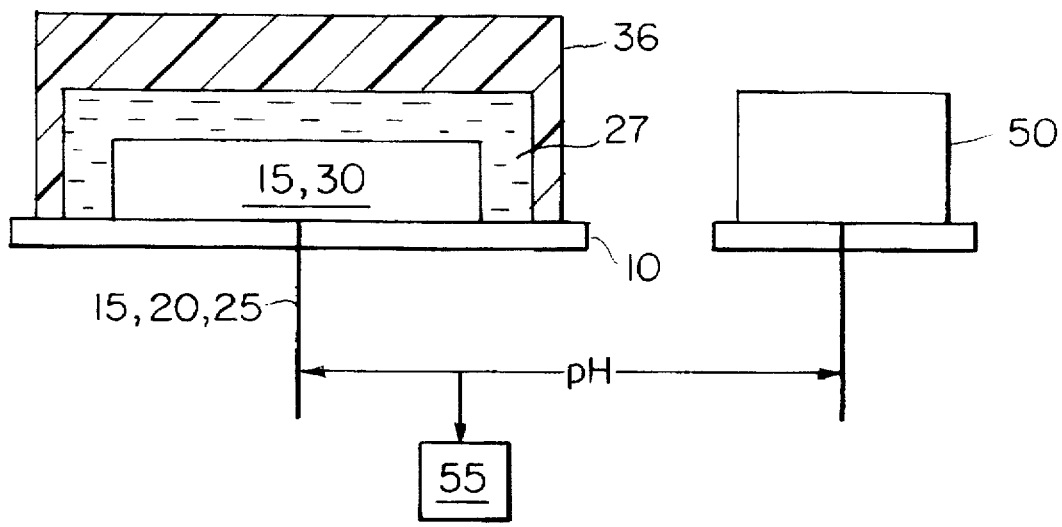
FIG. 6 shows a planar sensor with a metal/metal oxide electrode covered by an internal electrolyte layer and a neutral carrier cover membrane placed on top the electrolyte and a reference electrode.

FIG. 6 shows a sensor formatted such that an internal electrolyte 27 is superimposed over active electrode region 15, 30 and neutral carrier cover membrane 36 is superimposed over the internal electrolyte layer 27. The internal electrolyte typically functions to keep the pH constant in the proximity of the electrode(s) and may be buffered if desired. Buffers that may be included are well known in the art.

Figure 7:
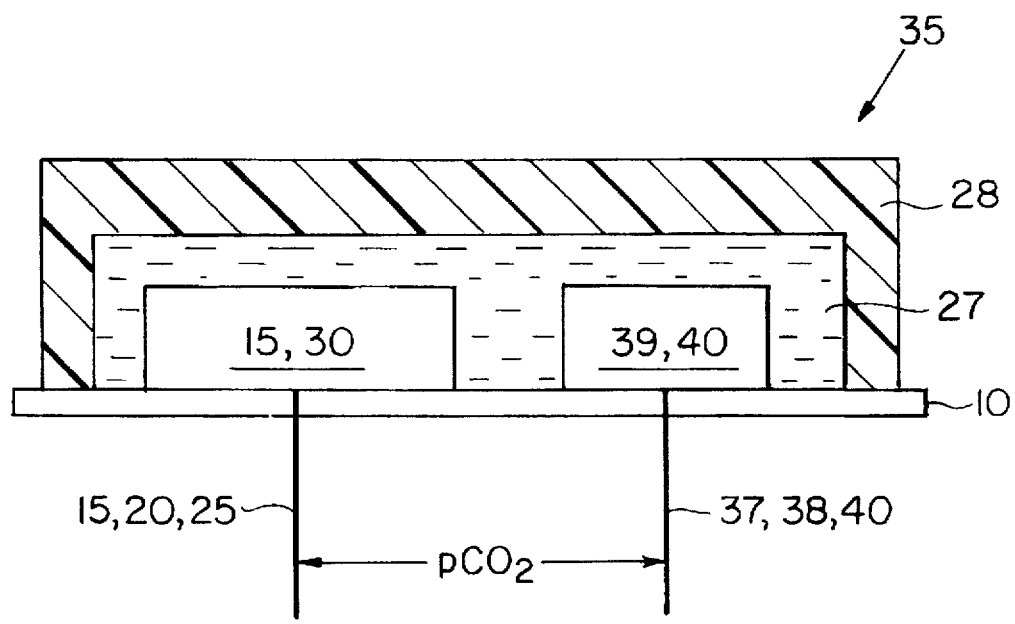
FIG. 7 shows a Severinghaus $CO_2$ type sensor.

FIG. 7 shows a $CO_2$ Severinghaus type of sensor having present a metal/metal oxide electrode area 15, 30 and a silver/silver halide internal reference electrode area 39, 40. As shown, the $CO_2$ permeable membrane 28 is superimposed over the internal electrolyte 27. The $CO_2$ permeable membrane 28 is not permeable to acid and separates the sample from the sensor. The permeable membrane 28 may be applied to the sensor by various techniques including dip coating, and so on. Materials that may be used include polymeric and copolymeric materials, as well known in the art. In the Severinghaus sensor, the internal silver/silver halide reference electrode provides a stable reference potential. A bicarbonate fill solution is typically utilized as the internal electrolyte 27 prior to usage. As $CO_2$ from the sample diffuses through the membrane and reaches an equilibrium, the pH of the bicarbonate fill solution changes, and is detected by the sensor. The change in the pH is related to the log of the partial pressure of $CO_2$.

In addition to using the metal/metal oxide component in the above-described pH and $CO_2$ sensors, other sensor systems may also incorporate the metal/metal oxide electrode, as may be accomplished by techniques known to those skilled in the art. The various components of the sensors are adheringly applied to the substrate by known techniques. For example, the electrically conductive material is preferably heated on the substrate prior to applied the metal paste mixture (and silver/silver halide material). Additionally, the silver/silver halide is preferably heated on the substrate after application to the conductive region. The dielectric coating may be heated/and or dried. The various membranes are typically dried and/or heated onto the substrate.

It is to be understood that various modifications to the invention will be apparent to and can readily be made by those skilled in the art, given the disclosure herein, without departing from the scope and materials of this invention. It is noted that the following examples given herein are intended to illustrate and not to limit the invention thereto.

EXAMPLES

Figure 8:
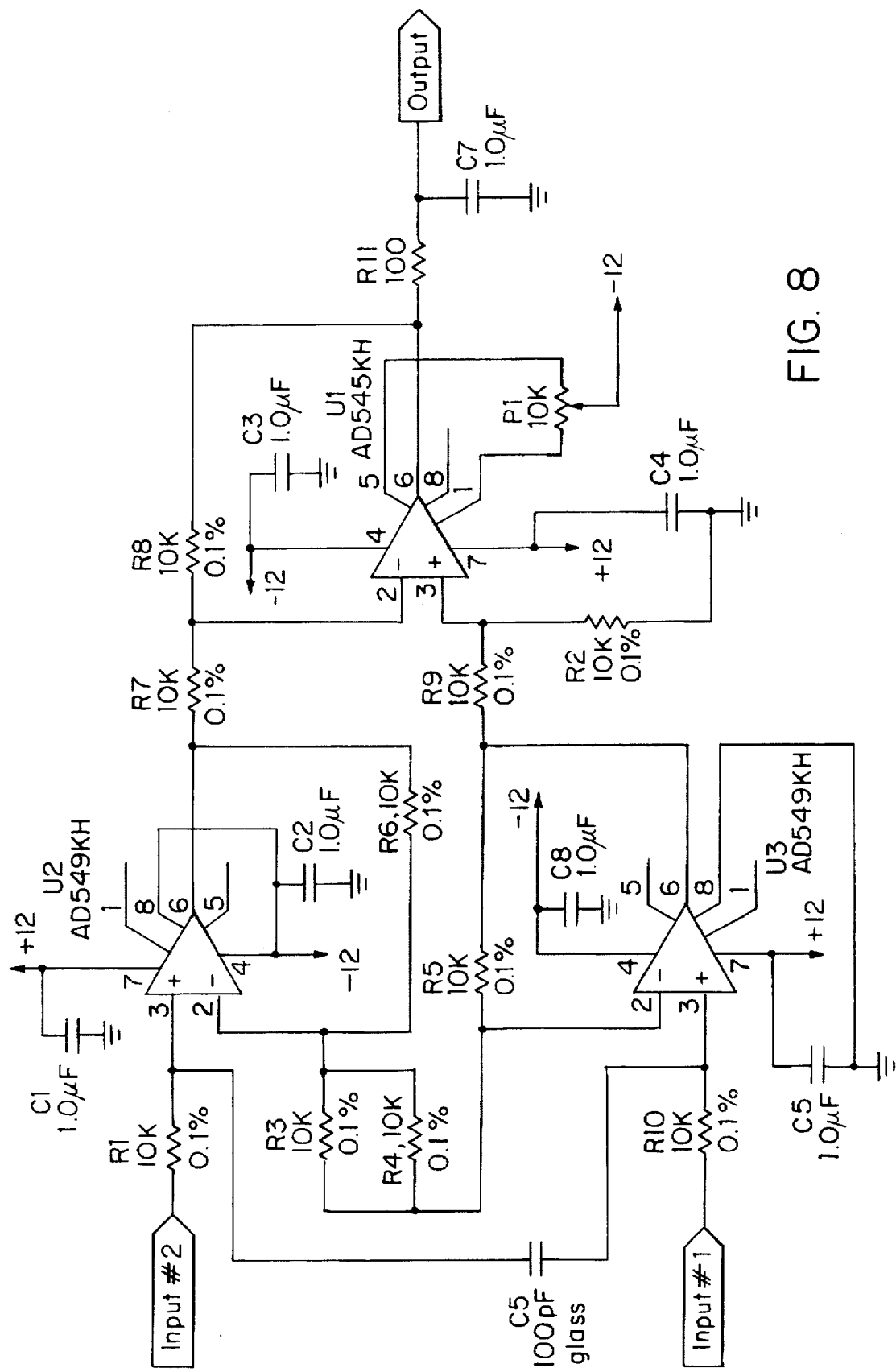
FIG. 8 shows the electrical circuitry used in the Examples section.

The electrical circuitry utilized for the all of the examples is shown in FIG. 8. Further description of circuitry may be found in *Ion-Selective Electrode Methodology*, Vol. I, Ed. Arthur K. Covington, CRC Press, 1979, pp. 32–33. (hereby incorporated by reference). Three dimensional, flow-through glass pH sensors ("Type A") were used as standards (as available from Ciba Corning Diagnostics Corp., Medfield, Mass., 278 series), as identified as sensor Type "A". Three other types of sensors (all planar) were prepared and are identified as Types "B", "C" and D". A silk screen printing technique was used in the fabrication of the planar sensors in the format shown in FIG. 3. As shown in FIG. 3, a metal/metal oxide and a Ag/AgCl electrode were present on the substrate chip, however, in the present set of examples, the Ag/AgCl electrode was not used, rather a Ag/AgCl external reference was used.

The substrate chips upon which each type of planar sensors were fabricated were 2" by 2" wafers perforated to form a total of 40 sensors. The wafers were made of approximately 96% alumina and approximately 4% glass binder, as purchased from Coors Ceramic Company, Grand Junction, Colo. As shown in FIG. 3, a gold (Au) electrically conductive region was applied to 15, 20, 25. Parallel to this strip, a gold strip was applied to region 37 and the upper portion of 38. The lower region of 38 continuous to and including 39 had applied thereto a silver paste (obtained from Metech, Elverson Pa.). The gold was purchased from E.I. DuPont DeNemours & Company of Wilmington, Del. Upon depositing the conductive regions on the substrate chips 10, the chips were heated at 850° C. for 6 minutes. A dielectric insulating material 26 (Cat. No. 9615 from E.I. DuPont DeNemours & Co.) was applied over the substrate and conductive regions with the exception of an exposed first portion 15 and 25 on the first gold strip and an exposed second region 39 and 37 on the second strip. The chips were then reheated at 850° C. for 6 minutes. Thereafter, the different metal pastes, as described below, were applied to the other gold strip in the exposed electrode area. A preformed Ag/AgCl electrode plating was deposited on the exposed silver region 39 to go to form the internal reference region 40.

In the Type B and D sensors (both representing the INVENTION), the metal paste was a base and metal paste mixture prepared by mixing approx. 5 g of palladium paste (purchased as Catalogue No. PC10141 from Metech Company of Elverson, Pa.) and approx. 1 g of $NaHCO_3$ (fine powder particulate). In the Type C sensor chips (representing a COMPARATIVE), the metal paste applied to the gold strip was an already formed palladium oxide paste purchased from Metech under Catalogue No. PC10119.

The metal paste was applied to the exposed electrode area 15 of the gold strip on the substrate by silk screening and thereafter the entire chip was then heated at about 550° C. for approx. 10 min. in the presence of air, thereby forming the Pd/Pd oxide active electrode.

Figure 2B:
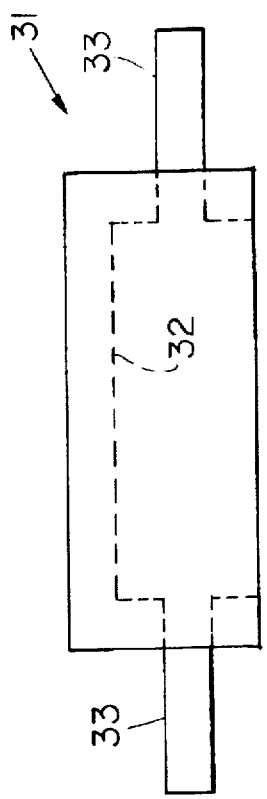

The Type D sensor chips differed from Type B sensors by the Type D sensors having an internal electrolyte layer adjacent to the electrodes as well as a neutral carrier cover membrane superimposed over the internal electrolyte layer, as shown in FIG. 6. The internal electrolyte layer was prepared as a coating using a solution formed by first dissolving approx. 2% wt./vol. of 100% hydrolyzed polyvinyl alcohol in 100 ml of water and thereafter adding 0.8 ml of a 0.1M solution of $NaHCO_3$ and KCl. This coating solution was then deposited over beth the active electrode and the silver electrode on the chip. Thereafter, the material was dried at 80° C. for about 1 hour thus forming the internal electrolyte layer on the chip. A cover membrane was then applied on top of the internal electrolyte membrane. The cover membrane was a polymer solution in 5% wt./vol. tetrahydrofuran of 68.9 wt. % dioctyl phthlate (a plasticizer), 26.0 wt.% polyvinyl chloride (PVC), 3.1 wt. % (TDDA, ioniphore for pH), 2 wt. % potassium tetra (p-chloro phenyl) berate (KTpClPB). An aliquot of this solution was spread evenly over the entire chip and the solvent allowed to evaporate to form the PVC-based cover membrane. When electrical contact was made between the Type D sensors and the sensing instrument, the cover membrane was scratched off the electrical contact area 25 prior to usage. Acrylic sample chambers, as shown and described in FIG. 2 were employed for all planar sensors used.

Example 1

This example demonstrates a linear mV response of the standard glass sensors (Type A) and two types of the planar sensors (Types B and C) when tested in aqueous solution containing bicarbonate. Variations in pH level were produced by varying the percent of $CO_2$ in solution and the concentration of bicarbonate, with the solution kept at approx. 37° C. Carbon dioxide was used to generate the pH values. The $O_2$ levels were also varied with the $CO_2$ levels to test for $O_2$ interference. A total of three different pH conditions and levels of $CO_2$ gas in aqueous samples containing bicarbonate were tested.

Figure 9:
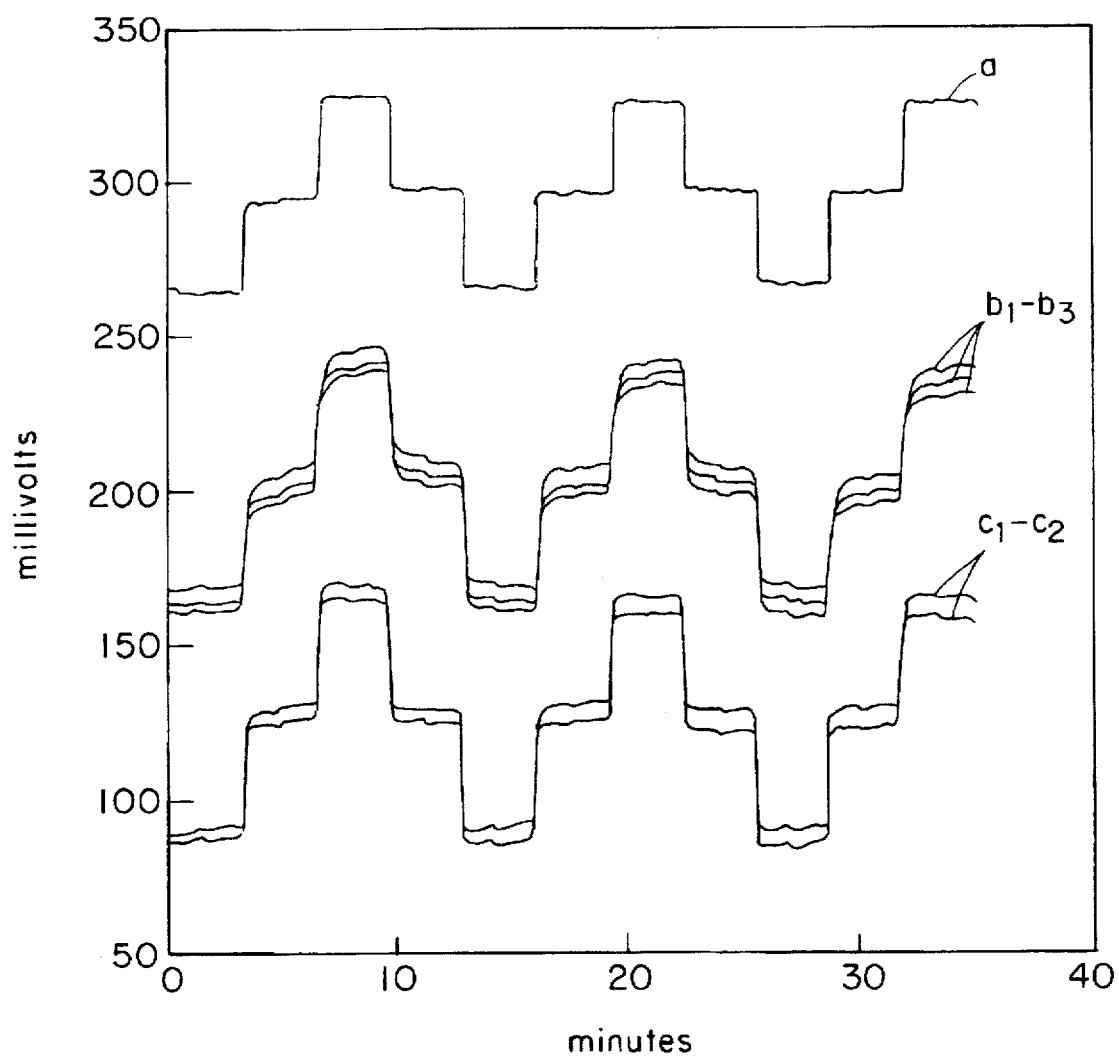
FIG. 9 is a pH response curve, as described in Example 2, where line a is from a glass sensor (Type "A", STANDARD, lines $b_{1-3}$ are from planar sensors (Type "B", INVENTION) and lines $c_{1-2}$ are from planar sensors (Type "C", COMPARATIVE).

The output of the pH sensors was measured as the potential (volts) between the active electrode and an external reference. The mV output of the sensors-was measured, with results summarized in TABLE I below and illustrated in FIG. 9. As shown in the figure, line a is the mV output from the glass sensors (Type A), lines $b_{1-3}$ are from the Type B planar pH sensors (INVENTION), and lines $c_{1-2}$ are from the Type C planar pH sensors (COMPARATIVE). Results indicated that all sensors provided adequate slopes and linearity to give acceptable measurement for pH.

TABLE I

| | pH Linearity | | | | | |
|---|---|---|---|---|---|---|
| SENSOR | TYPE A | TYPE B | TYPE B | TYPE B | TYPE C | TYPE C |
| SLOPE | −60.87 | −74.03 | −73.06 | −73.62 | −73.94 | −72.94 |
| Rsq. | 0.9998 | 0.9995 | 0.9995 | 0.9995 | 0.9997 | 0.9998 |

Example 2

The mount of oxygen ($O_2$) was varied to test for drift induced by the changes in oxygen levels (i.e. $O_2$ interference). The pH and $CO_2$ present were kept at a constant 3% during all tests.

Figure 10:
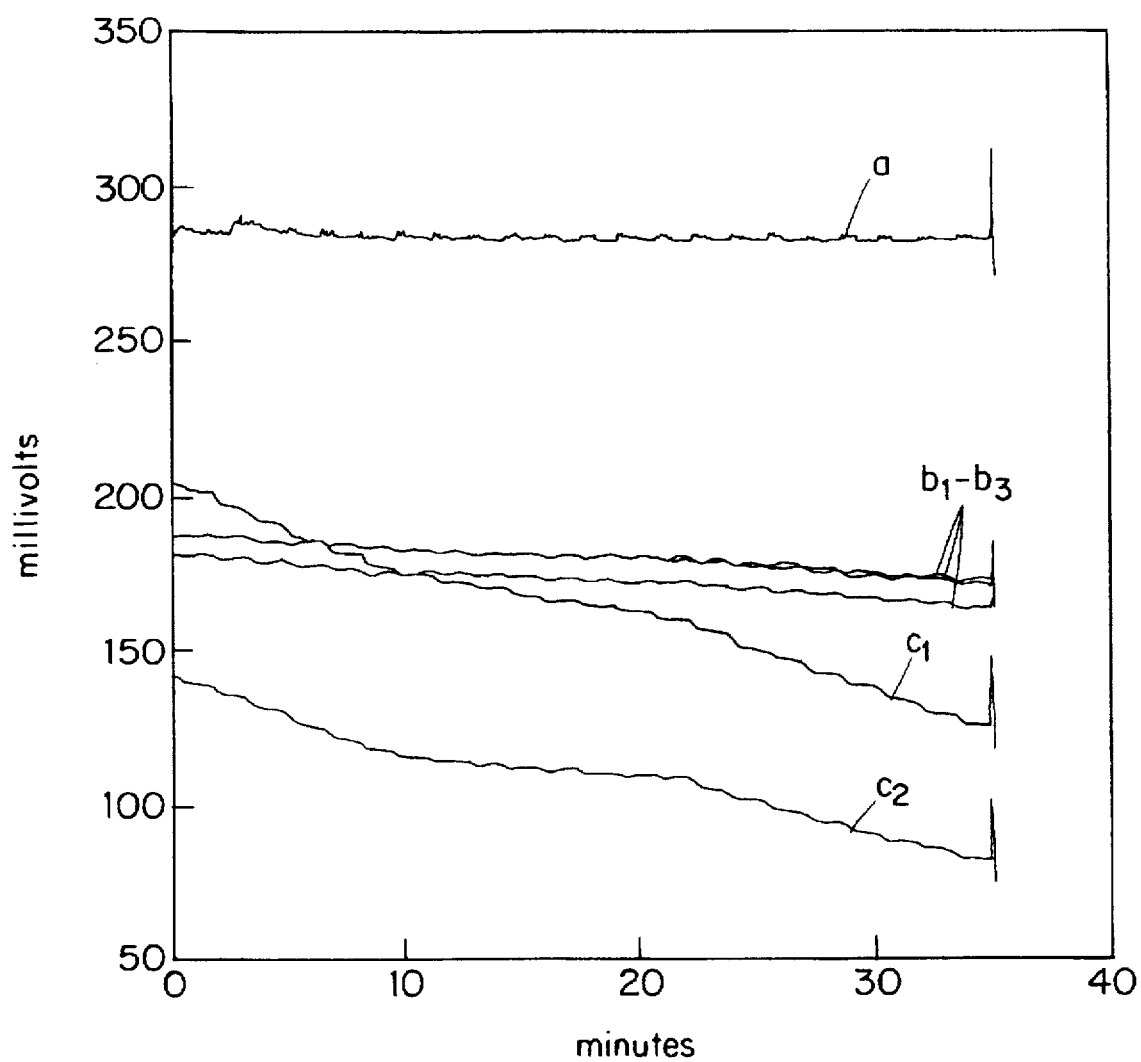
FIG. 10 is a pH response curve, as described in Example 3, where line a is from a glass sensor (Type "A", STANDARD), lines $b_{1-3}$ are from planar sensors (Type "B", INVENTION), and lines $c_1$ and $C_2$ are from planar sensors (Type "C", COMPARATIVE).

As shown in FIG. 10, a Type A glass sensor (line a) was tested as well as three Type B planar sensors (INVENTION, lines $b_{1-3}$) and two Type C planar sensors (COMPARATIVE, lines $c_{1-2}$). The data show little to no response changes in the output of the Type B sensors in going from 0 to 26% $O_2$ (at constant 3% $CO_2$). In contrast, the Type C sensors show undesirable drifts in the mV output induced by the changes in $O_2$ levels, i.e. $O_2$ interference.

Example 3

Figure 11:
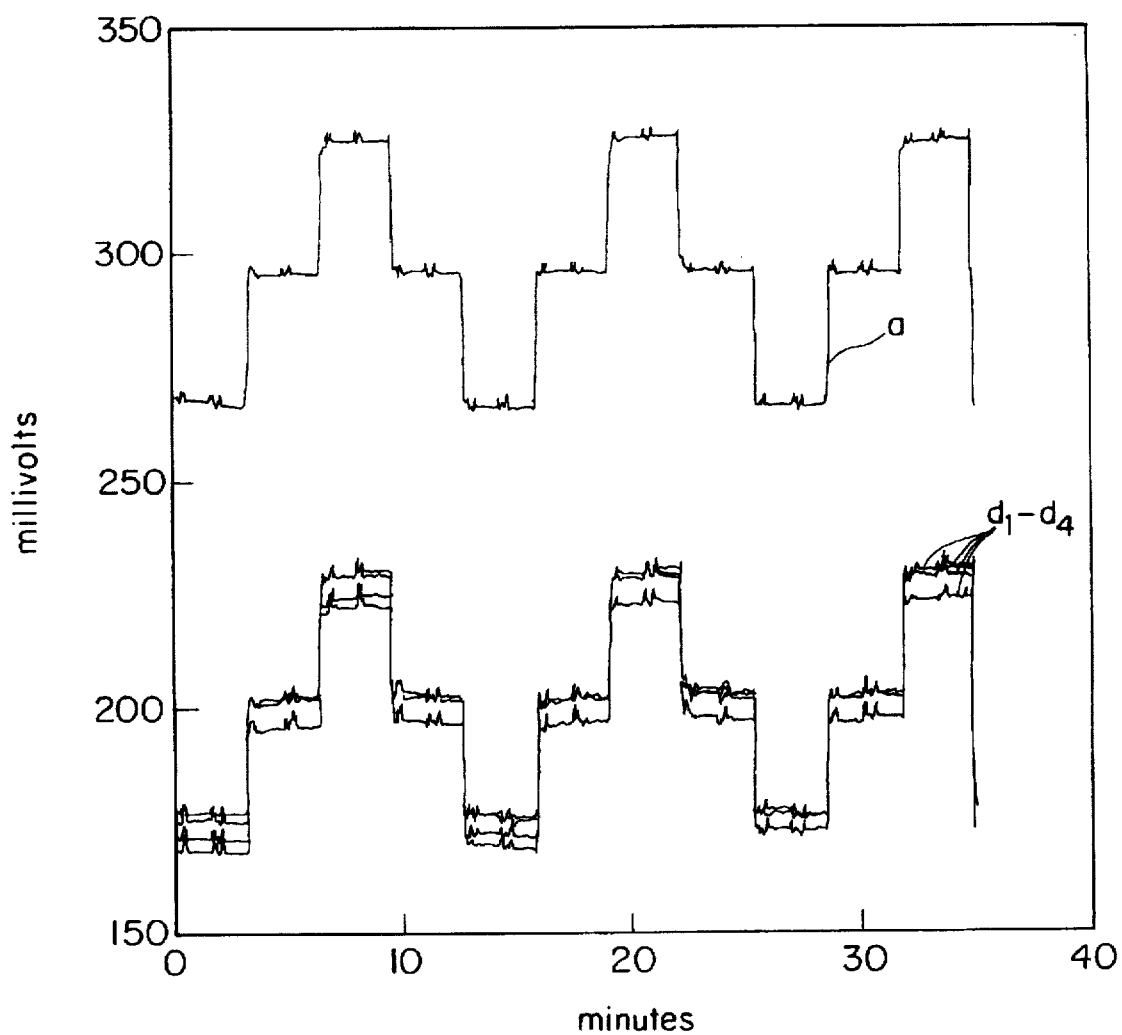
FIG. 11 is a pH response curve, as described in Example 4, where line a is from a glass sensor (Type "A", STANDARD) and lines $d_{1-4}$ are from a planar sensor (Type "D", INVENTION).

Using the Type D planar sensors (INVENTION), samples at three different pH conditions were tested. Type A glass sensors were also tested under the same conditions to provide a standard, with the method of collecting data as described in Examples 1 and 2. Results are summarized in TABLE II and illustrated in FIG. 11. As shown, the Type D planar sensors provided comparable slopes and linearity as those provided by the standard.

TABLE II

| | pH Linearity | | | | | |
|---|---|---|---|---|---|---|
| SENSOR | TYPE A | TYPE D | TYPE D | TYPE D | TYPE D | TYPE D |
| SLOPE | −61.9 | −54.6 | −56.9 | −56.8 | −58.4 | −53.5 |
| Rsq. | 0.99995 | 0.99986 | 0.99984 | 0.99994 | 0.99992 | 0.9998 |

It is not intended that the scope of the claims appended hereinafter are limited to the description as set forth herein, but rather that the claims be construed as encompassing all features of patentable novelty which reside in the present invention, including all features which would be treated as equivalents thereof by those skilled in the art to which the invention pertains.

That which is claimed is:

1. A method for preparing a planar active metal/metal oxide electrode, said method comprising combining a base component consisting essentially of a salt with a metal paste to form a metal paste mixture, heating the metal paste mixture in the presence of air for a time sufficient to cause said heat to oxidize a portion of the mixture to form said metal/metal oxide electrode.

2. A method according to claim 1 wherein said salt is non-hydroscopic.

3. A method according to claim 1 wherein said metal paste is a palladium paste.

4. A method according to claim 3 wherein said base component is $NaHCO_3$.

5. A method according to claim 1 wherein said heating occurs at a temperature of from about 450° C. to 600° C. for a period of from about 1 minute to about 30 minutes.

6. A method according to claim 5 wherein said metal is a noble metal selected from the group consisting of palladium, rhodium, ruthenium, osmium, iridium, platinum, tin, antimony, bismuth, alloys thereof, and mixtures thereof, and said base component is a salt selected form the group consisting of alkali metal salts and alkali earth metal salts.

7. A method according to claim 6 wherein said metal paste is a palladium paste, and said base component is $NaHCO_3$.

8. A method according to claim 7 wherein heating is at a temperature of 525° C. to 575° C. for a period of about 5 minutes to 15 minutes and said salt is present in an amount ranging from about 0.1 wt. % to about 50 wt. %, based on the total weight of the mixture prior to heating.

9. A method according to claim 8 wherein said salt present in an amount of about 16 wt. %.

* * * * *